US 6,645,225 B1

(12) United States Patent
Atkinson

(10) Patent No.: US 6,645,225 B1
(45) Date of Patent: Nov. 11, 2003

(54) METHOD AND APPARATUS FOR PLUGGING A PATENT FORAMEN OVALE FORMED IN THE HEART

(76) Inventor: Alvan W. Atkinson, 1505 Old Crews Rd., Knightdale, NC (US) 27545

( * ) Notice: Subject to any disclaimer, the term of this patent is extended or adjusted under 35 U.S.C. 154(b) by 290 days.

(21) Appl. No.: 09/704,915

(22) Filed: Nov. 1, 2000

(65) Prior Publication Data (65)

(51) Int. Cl.[7] ............................................. A61B 17/08
(52) U.S. Cl. ..................................... 606/213; 128/898
(58) Field of Search ............................... 606/213, 194, 606/73, 95, 104; 623/23.48, 2.1, 904; 604/167.01, 167.03, 238, 907; 4/295, 286; 215/355, 356; D09/439; 128/898, 846

(56) References Cited

U.S. PATENT DOCUMENTS

| 5,192,301 A | * | 3/1993 | Kamiya et al. ............. 606/213 |
| 5,425,757 A | * | 6/1995 | Tiefenbrun et al. ......... 606/194 |
| 5,645,565 A | * | 7/1997 | Rudd et al. ................. 606/213 |
| 6,016,806 A | * | 1/2000 | Webb ........................ 128/846 |

* cited by examiner

Primary Examiner—Michael J. Milano
Assistant Examiner—Julian W. Woo
(74) Attorney, Agent, or Firm—Coats & Bennett, P.L.L.C.

(57) ABSTRACT

A percutaneous catheter based method and apparatus for removably plugging a Patent Forman Ovale (PFO) in a patient's heart deploys a threaded surgical plug into the PFO. The plug is removably connected to a flexible connector. The plus is deployed in the PFO by advancing it through a catheter and rotating it into the PFO, then disengaging the flexible connector. The plug may be optionally removed by re-engaging the flexible connector and rotating the plug out of the PFO.

43 Claims, 11 Drawing Sheets

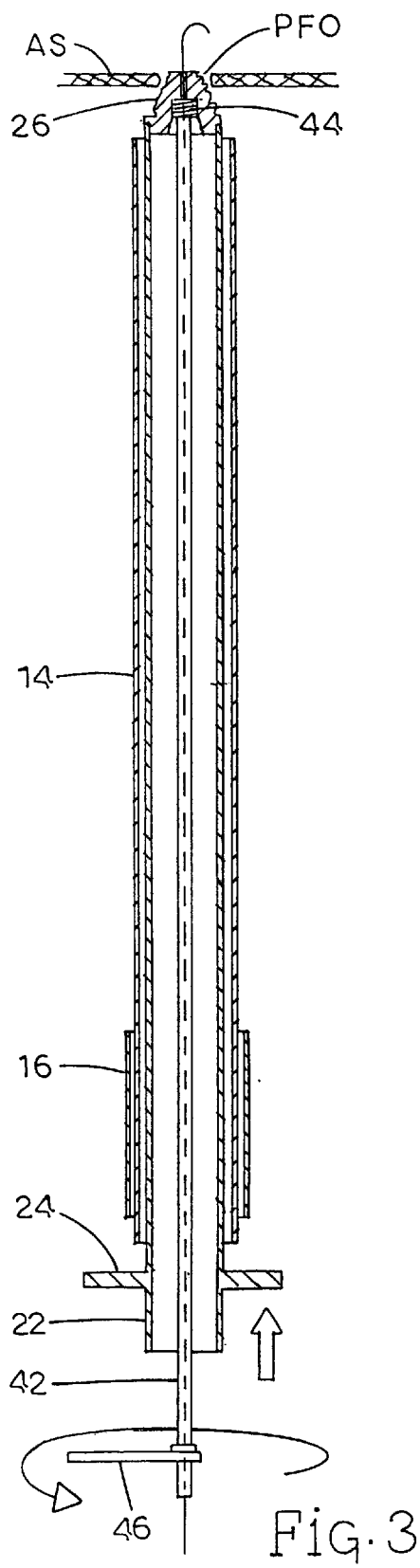
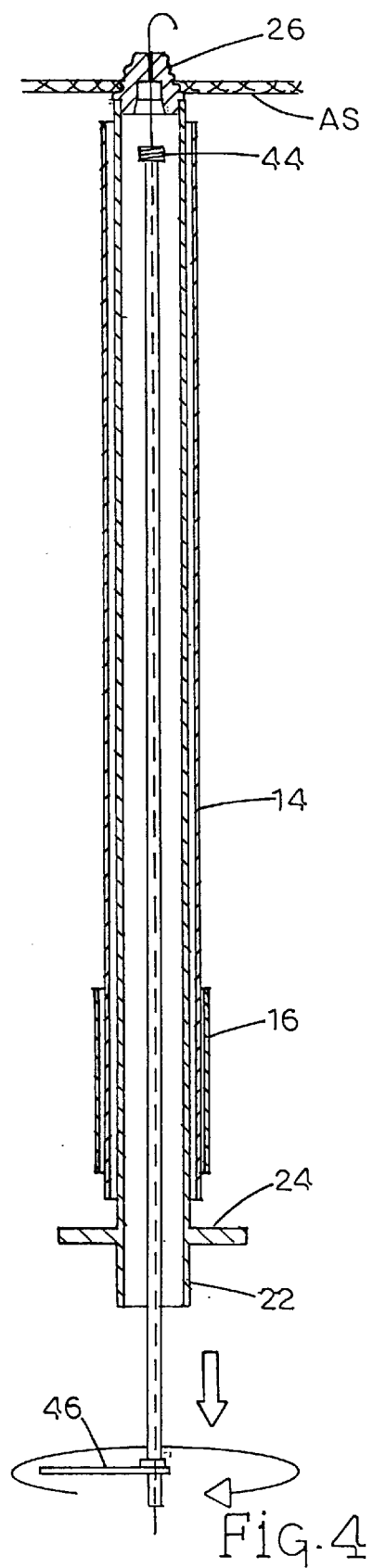

METHOD AND APPARATUS FOR PLUGGING A PATENT FORAMEN OVALE FORMED IN THE HEART

FIELD OF THE INVENTION

The present invention relates to a percutaneous catheter based method and apparatus for plugging a Patent Foramen Ovale formed in the heart of a human.

BACKGROUND OF THE INVENTION

The human cardio-pulmonary system, for oxygenating and circulating blood throughout the body, is dramatically different between normal adults and fetuses. In the adult circulatory system, blood is pumped from various parts of the body to the right side of the heart, and then through the pulmonary artery to the lungs. Following oxygenation at the lungs, the blood travels through the pulmonary veins to the left side of the heart, and is pumped from there through the aorta to the brain and other parts of the body.

During gestation, human fetuses do not breathe air. Rather, their blood is oxygenated by maternal blood through the placenta. Hence, not only is there no great need to divert all blood to the lungs upon every trip through the circulatory system, but additionally the fact that the lungs are collapsed makes it difficult for blood to flow and significantly raises the pressure in the pulmonary path of the circulatory system. To bypass the unnecessary trip to the lungs, blood in the fetal heart is shunted directly from the right chamber into the left chamber of the fetal heart through a valve-like opening in the wall separating the two sides of the heart, known as the Foramen Ovale. The blood is then pumped from the left side of the heart into the aorta and directly to the brain and other points in the fetal body.

After birth, the cardio-pulmonary system changes significantly. The lungs fill with air, reducing the resistance to blood flow through the lungs, and thus dramatically decreasing the pressure of the pulmonary path, i.e., the pulmonary artery and the right side of the heart. In this condition, the left side of the heart is maintained at a somewhat higher pressure than the right side, and the valve-like Foramen Ovale is forced closed, sealing off blood flow between the two sides of the heart. Eventually, fibrous tissue covers the closed Foramen Ovale and permanently seals it off. However, in twenty-five percent to thirty-five percent of adults, the Foramen Ovale remains open, or "patent." This allows un-oxygenated blood to flow directly from the right side of the heart into the left side, where it is carried through the aorta directly to the brain and other parts of the body. This shunting of the blood directly from the right to the left side of the adult heart, thus by-passing its trip to the lungs, can occur whenever the pressure in the right side of the heart exceeds that in the left. This condition occurs upon heavy lifting or at other times of great physical exertion, or during a Valsalva maneuver (an abdominal constriction performed while holding one's breath).

Not only does the mixing of un-oxygenated blood with oxygenated blood dramatically reduce the efficiency of the cardiopulmonary system, it is believed to contribute to life-threatening ischemic strokes through paradoxical embolism. When blood clots in veins break off, or embolize, they normally travel through the right side of the heart and to the lungs, which act as a filter. The clots are thus normally filtered from the arteries, in particular the aorta and carotid arteries leading to the brain. In a paradoxical embolism, clots pass from a vein into an artery, such as through a Patent Foramen Ovale (PFO) or other atrial septal defect. If carried to the brain, the clots can obstruct the arterial blood supply, leading to an ischemic stroke. Once detected, the PFO condition requires either a regimen of anti-coagulants to prevent further clots, or closing of the PFO.

The traditional method of closing a PFO is open-heart surgery. This is expensive, complex, involves significant risk due to general anesthesia, infections, etc., and requires an extensive and painful recovery period. Catheter-based methods of closing a PFO are known in the art. Typically, these catheter-based solutions comprise a collapsed, expandable, or inflatable sealing element. The element is transferred through the catheter in a collapsed state, and is expanded upon deployment at the PFO within the heart. Such prior art devices typically deploy an expandable element on either side of the PFO, i.e., with a portion in both the left and right sides of the heart. Once deployed, the element is detached from the catheter and the catheter is withdrawn, leaving the element permanently in place. These prior art systems are deficient in that they depend on proper mechanical deployment of an element from a collapsed to an expanded state once positioned within the heart. If the element does not deploy, or deploys in an incorrect manner, it must be recompressed and withdrawn. Also, once inserted, the element is difficult or impossible to remove, since it has expanded on both sides of the PFO and cannot be removed.

SUMMARY OF THE INVENTION

The present invention entails a method of plugging or sealing a Patent Foramen Ovale (PFO) formed in the heart. The method entails inserting a threaded plug into the PFO and rotating the threaded plug and securing the threaded plug in the PFO.

As embodied in one particular surgical procedure, the method further entails directing a guide wire into the heart and the PFO, and inserting a catheter over the guide wire and extending the catheter towards the PFO. Thereafter the threaded plug is secured to a carrier and the guide wire is threaded through both the carrier and the threaded plug. Thereafter, the carrier and threaded plug are moved towards the PFO. After the threaded plug has been secured within the PFO, the threaded plug is decoupled from the carrier. In one particular methodology of carrying out the above surgical procedure, a first member or flexible connector is secured to the threaded plug and both the carrier and the first member remain connected or secured to the threaded plug as it is advanced towards the PFO. In this particular embodiment of the invention, the first member or flexible connector is disconnected from the threaded plug first. Thereafter, the threaded plug is urged from the carrier.

In addition, the present invention entails a surgical kit for plugging or sealing an opening in the heart. The surgical kit includes a threaded plug adapted to be secured into the opening of the heart. Further, the surgical kit includes a carrier for holding the threaded plug and for delivering the threaded plug to the opening in the heart. Finally, the surgical kit includes a catheter for receiving the carrier and the threaded plug and permitting the carrier and the threaded plug to be moved through the catheter to the opening in the heart.

Finally, another aspect of the present invention entails a threaded plug for plugging an opening in the heart. The threaded plug basically comprises a tip and a circumferential lip spaced from the tip and adapted to lie adjacent the heart tissue surrounding the opening in the heart. There is provided a threaded portion disposed generally between the tip and the circumferential lip that includes a surrounding thread pattern formed on the outer surface of the threaded plug. The opening in the heart is plugged or sealed by rotating or screwing the threaded plug into the opening.

BRIEF DESCRIPTION OF THE DRAWINGS

FIG. 3 is a section view of the :surgical kit of the present invention, depicting the insertion of the plug;

FIG. 4 is a section view of the surgical kit of the present invention, depicting the removal of the flexible connector;

DETAILED DESCRIPTION OF THE INVENTION

In one embodiment, the present invention comprises a surgical kit, indicated generally by the numeral 10, for the minimally invasive, percutaneous introduction and deployment of a Patent Foramen Ovale (PFO) plug 26. Plug 26 is introduced and deployed via a catheter, eliminating the need for open-heart surgery. The surgical kit 10 is depicted in the accompanying drawings, with its various constituent parts and configurations, in FIGS. 1 through 8.

Figure 1:
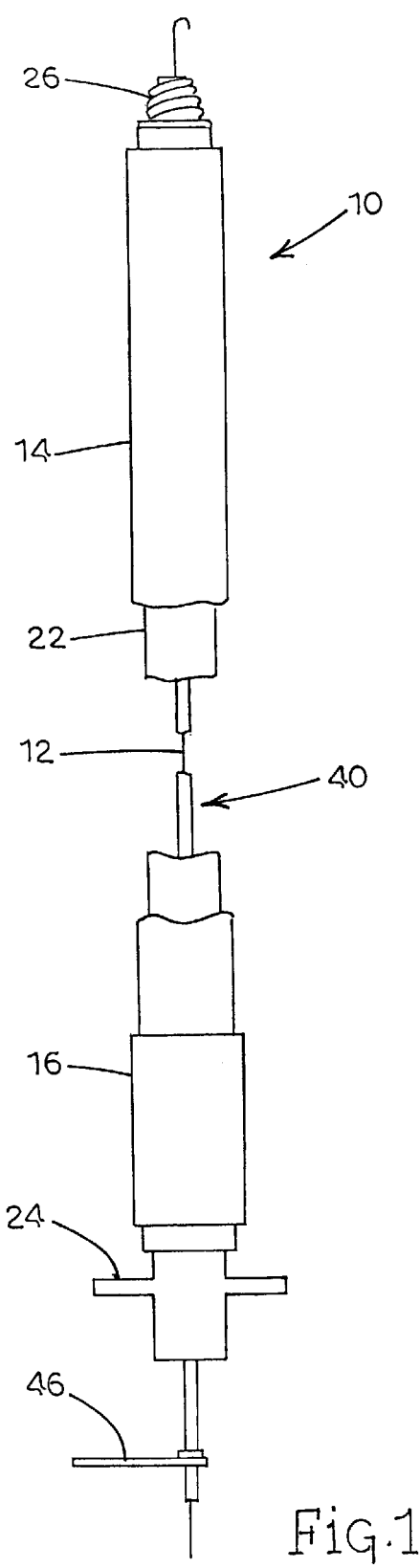
FIG. 1 is a cut-away view of the surgical kit of the present invention.
Figure 1A:
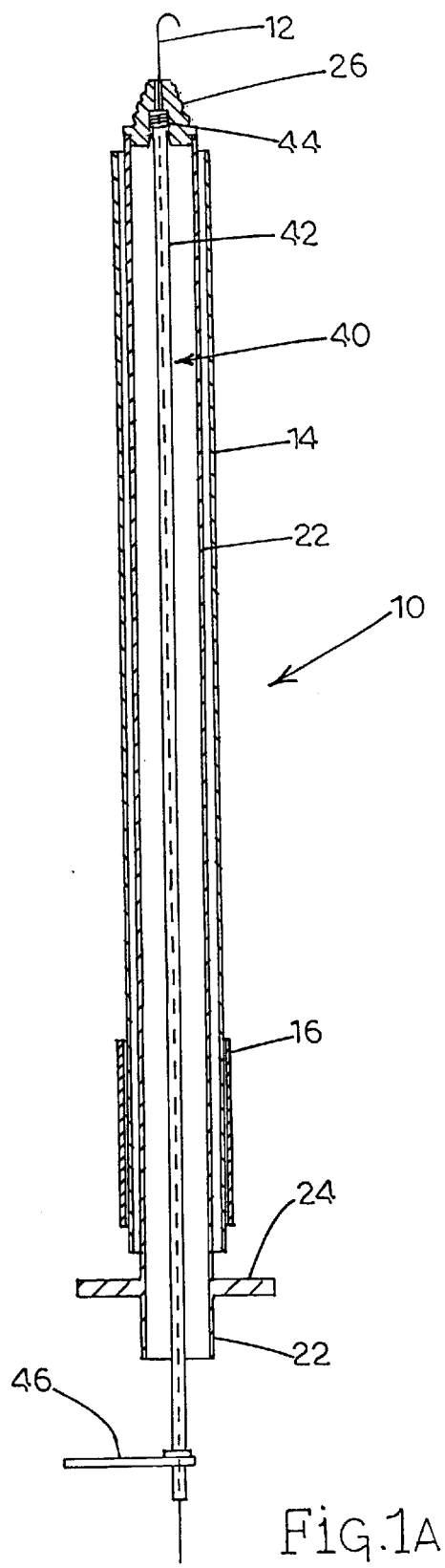
FIG. 1a is a section view of the surgical kit of the present invention.
Figure 5:
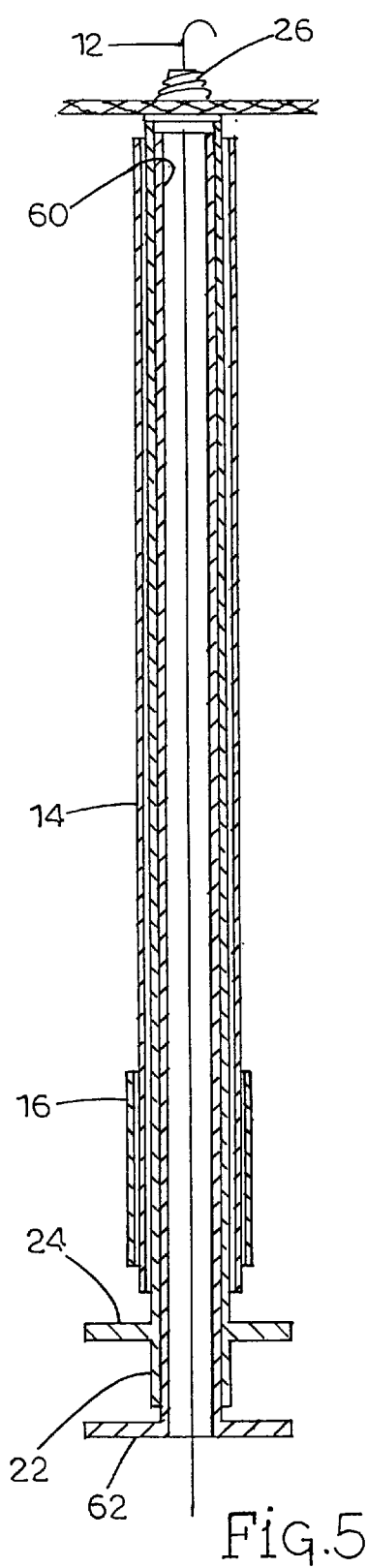
FIG. 5 is a section view of the surgical kit of the present invention, with the plunger installed.
Figure 6:
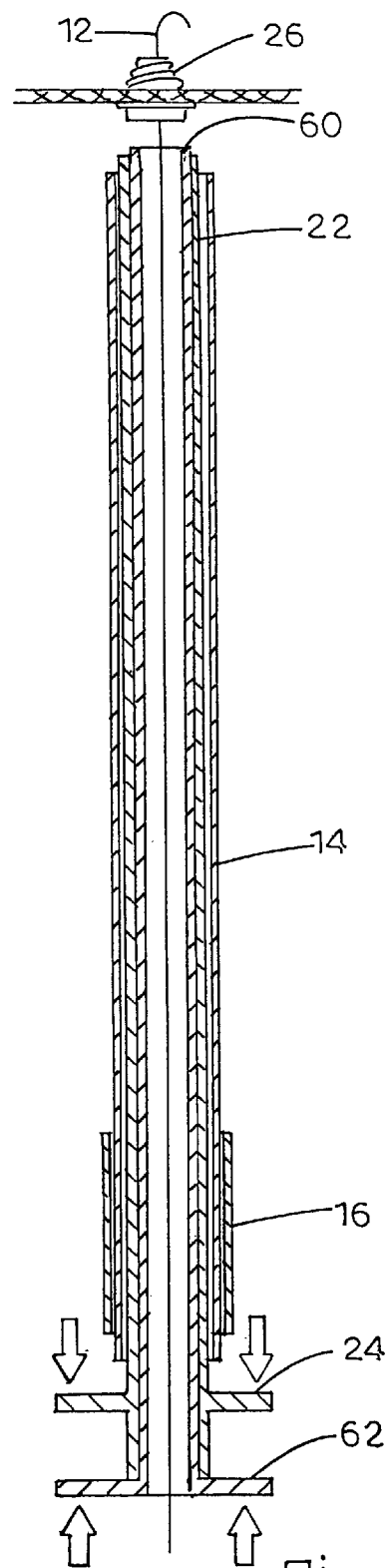
FIG. 6 is a section view of the surgical kit of the present invention, depicting the disengagement of the plug by the plunger.
Figure 7:
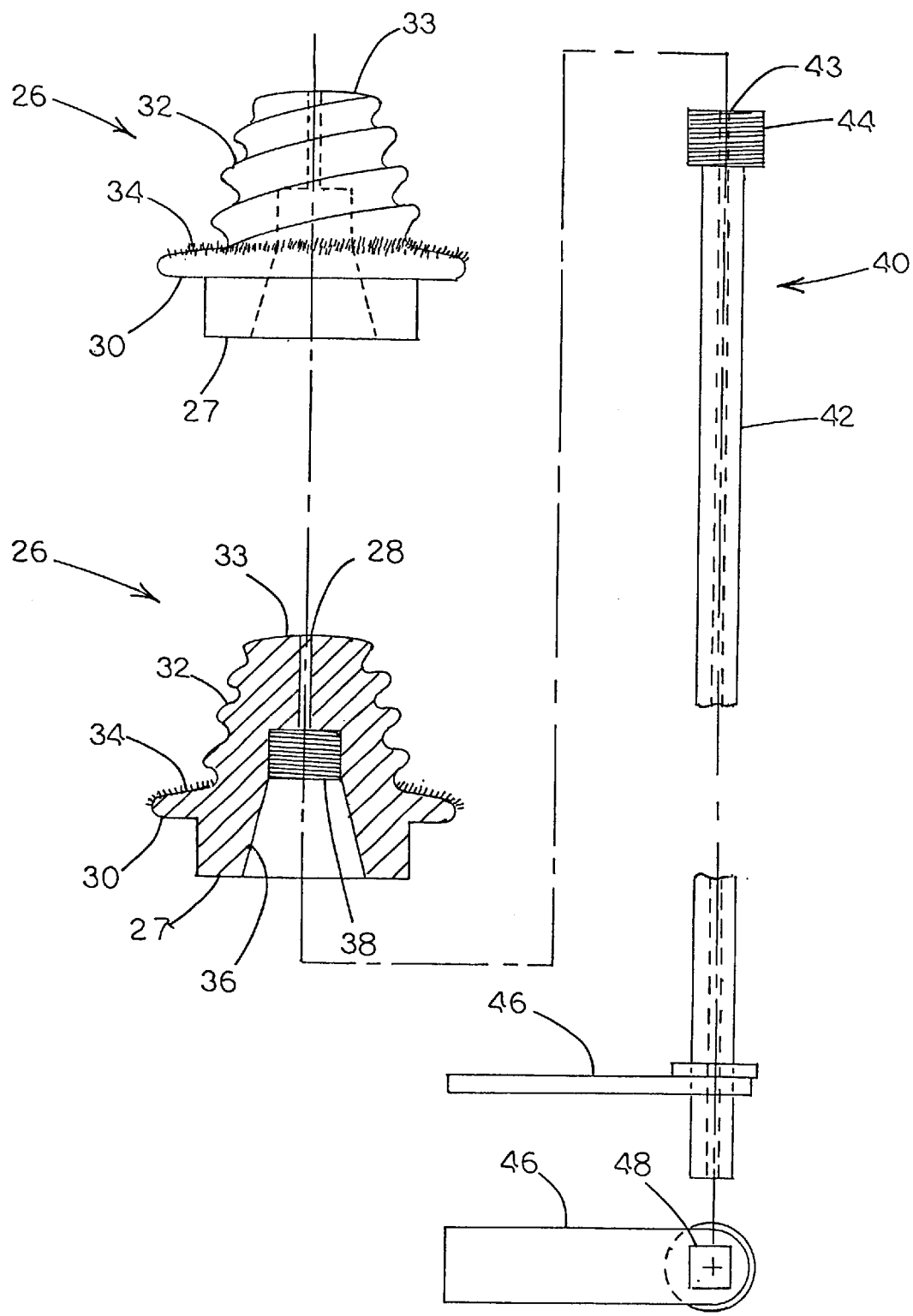
FIG. 7 is a section view of the flexible connector, wrench, and plug, and a side view of the plug.

The surgical kit 10 for plugging a PFO includes the plug 26 as particularly illustrated in FIG. 7. To facilitate the delivery and securement of the plug 26 in the PFO, the surgical kit 10 may further include a J-wire 12, a dilator 16, a catheter 14, a plug carrier 22, a flexible connector 40 (sometimes referred to as a first member), and a tool or wrench 46 for manipulating the flexible connector 40 as shown in FIGS. 1 and 1A. Additionally, the surgical kit 10 may include a sizer 50, as particularly shown in FIG. 2, and a plunger 60 (sometimes referred to as a second member), as depicted in FIGS. 5 and 6. As will be appreciated from subsequent portions of this disclosure, the plug carrier 22 is adapted to receive and hold the plug 26, and to deliver the plug 26 to the site of the PFO. Additionally, the flexible connector is also adapted to be secured to the plug 26. Together, the plug carrier 22 and the flexible connector 40 remain secured to the plug 26 as the plug 26, is advanced through the catheter 14 towards the PFO. As will be further discussed, once the plug 26 is appropriately positioned adjacent the PFO of the heart, both the carrier 22 and flexible connector 40 are rotated, causing the plug to be screwed or secured within the PFO. Thereafter, both the plug carrier 22 and the flexible connector 40 are decoupled from the plug 26 and removed, along with the catheter, from the patient's body. The particulars of the decoupling procedure will be addressed subsequently herein.

Referring to the components of the surgical kit 10 and with particular reference to FIGS. 1 and 1A, the J-wire 10 is a thin, pliable wire formed of surgical steel or similar suitable material. During the procedure for plugging the PFO, the J-wire 12 is inserted into the patient's inferior vena cava at the right groin, and inserted through the inferior vena cava into the right atrium of the patient's heart, following well-known cardiac catheterization procedures. J-wire 12 is of solid material with sufficient density or other physical properties relative to the imaging technique used, e.g., x-ray fluoroscopy, ultrasound imaging, etc., that the J-wire 12 is readily discernable by the surgeon via the imaging system. In operation, the J-wire 12 provides guidance and alignment for the other elements of the surgical kit 10, as other elements are introduced into the patient's body and advanced to the patient's heart and to the PFO by sliding over the J-wire 12.

Dilator 16 is introduced into the patient's groin, and serves as a guide for the insertion and extraction of the remaining parts of the surgical kit 10. Catheter 14 is a tube of pliable material that is inserted through the dilator 16 and advanced through the inferior vena cava into the patient's right atrium, around and enclosing J-wire 12. It is contemplated that in normal applications, the catheter 14 is approximately 6 mm in diameter. The catheter 14, in addition to J-wire 12, serves as a guide for the insertion and extraction of the remaining components of the surgical kit 10. Specifically, all other components can be threaded over J-wire 12 and advanced within the bore of the catheter 14.

The plug carrier 22 serves to carry the plug 26 to the PFO in the patient's heart. The plug carrier 22 is a flexible tube that is deployed within the catheter 14 and around J-wire 12. The distal end of the plug carrier 22 is configured and adapted to receive the plug 26 is a press fit relationship. A press fit means that the inner diameter of the plug carrier 22 is approximately the same as the outer diameter of the base portion of the plug 26. When the plug 26 is inserted into the plug carrier 22, it is frictionally held in place. At the proximate end of plug carrier 22 are formed two finger tabs 24 extending radially therefrom on opposite sides. As used herein, the "proximate end" of surgical kit 10 or any component thereof refers to the end nearest the surgeon in use, i.e., the end that remains outside of the patient's body. Similarly, as used herein, the "distal end" of surgical kit 10 or any component thereof refers to the end that is deployed inside the patient's heart.

The plug 26, the flexible connector 40, and the wrench 46 are discussed with reference to FIG. 7, depicting elevation and sectional views of these components isolated from the rest of surgical kit 10.

The plug 26 is a surgical component that seals the PFO, and remains deployed within the patient's heart. Plug 26 comprises a base 27, a circumferential lip 30, a threaded portion 32, and a tip 33. The diameter of the plug 26 from the base 27 to the lip 30 is generally constant, and as described above, is approximately the same as the inner diameter of the distal end of the plug carrier 22. When the plug 26 is disposed within the distal end of the plug carrier 22, the portion of the plug 26 extending from the base 27 to the lip 30 is press-fitted within the plug carrier 22.

Figure 8A:
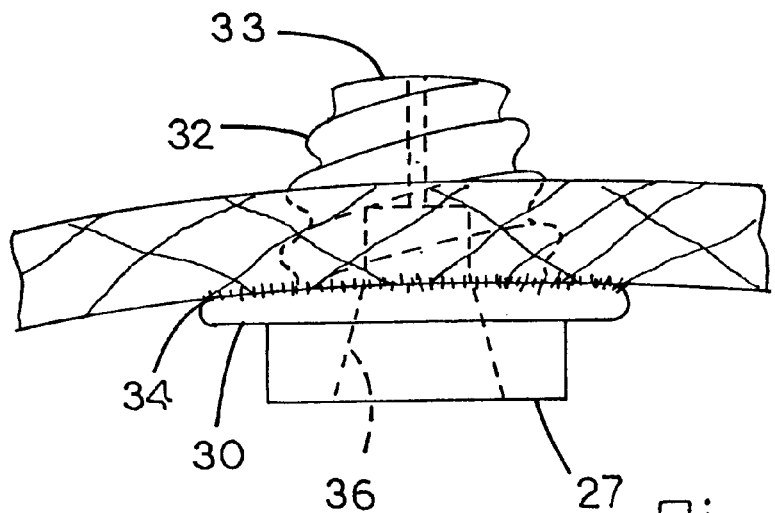
FIG. 8a is a section view of the plug immediately after insertion in the Patent Foramen Ovale.
Figure 8B:
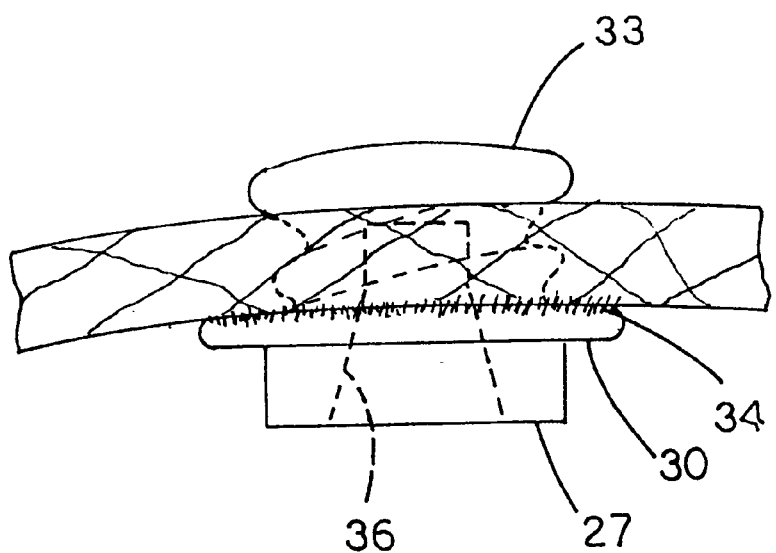
FIG. 8b is a section view of the plug following insertion in the Patent Foramen Ovale, depicting the plug tip swelling.

Between the circumferential lip 30 and the tip 33, is threaded portion 32. Along the extent of threaded portion 32, the diameter of the plug 26 gradually decreases from a maximum adjacent to the lip 30, to a smaller diameter at the tip 33. Additionally, shaped within the exterior of threaded portion 32 are approximately three to four turns of mechanical threads. When the plug 26 is deployed within the PFO and rotated by the surgeon, the threaded portion 32 of the plug 26 engages the tissue of the patient's cardiac septum, advancing the plug 26 into the PFO. Additionally, the threads on threaded portion 32 mechanically secure and retain the plug 26 in the patient's heart. In one embodiment, cilia 34 are formed in or disposed on the surface of circumferential lip 30 facing the threaded portion 32. When the plug 26 is fully deployed in the PFO, these cilia provide increased friction between the lip 30 and the patient's heart tissue, thus additionally securing the plug 26 by resisting rotation in the removal direction. The plug 26 may be formed of DACRON®, TEFLON®, or any suitable material. In one alternate embodiment, at least the tip 33 portion of plug 26 is hydroscopically expanding, i.e., it swells or volumetrically expands when exposed to water or other fluids. This property may help seal the plug 26 in the patient's PFO soon after its surgical insertion therein, as depicted in FIG. 8. FIG. 8A depicts the plug 26 of the present invention immediately following its insertion into a PFO in the patient's heart. The plug 26 has been advanced until the circumferential lip 30 is in contact with the tissue of the patient's cardiac septum. The tip 33 of the plug 26 extends through the PFO into the patient's left atrium. The subsequent swelling of the tip 33 is depicted in FIG. 8B.

Referring again to FIG. 7, formed within the base 27 of plug 26 is a conical retrieval aperture 36, which terminates in a tapped hole 38. Extending from the tapped hole 38 through the tip 33 of the plug 26 is center hole 28. The center hole 28 facilitates alignment of the plug 26 within the PFO, as the plug 26 is guided by the plug carrier 22 along J-wire 12, previously located within the PFO. Retrieval aperture 36 has a generally tapered conical shape leading to tapped hole 38. This shape facilitates the retrieval of the plug 26, if necessary, after its deployment in the PFO by guiding the flexible connector 40 to the tapped hole 38.

The flexible connector 40 comprises flexible connector shaft 42 and threaded end 44, with center hole 43 running throughout. The flexible connector 40 is disposed within the plug carrier 22, and is secured to the plug 26 by screwing the threaded end 44 into the tapped hole 38. Thus positioned, flexible connector 40 secures the plug 26 to the plug carrier 22 (in addition to the press-fit of the lower portion of the plug 26 within the distal end of the plug carrier 22). The flexible connector shaft 42 in the embodiment illustrated has a square cross-section, although a variety of other shapes are possible. Shaft 42 could, for example, be triangular, rectangular, pentagonal, hexagonal, star-shaped, etc. Wrench 46 contains a connector hole 48 of the same size and shape as the cross-section of flexible connector 42, for engaging and rotating the flexible connector shaft 42. It will be appreciated that any cross-sectional shape of flexible connector shaft 42 and corresponding connector hole 48 in wrench 46 capable of inducing torque on the flexible connector 40, as are well known in the art, will suffice and falls within the scope of the present invention. Referring back to FIGS. 1 and 1A, it will be noted that the flexible connector 40 extends past the proximate end of the plug carrier 22, to allow the engagement of wrench 46 with the flexible connector shaft 42. A center hole 43 extends throughout the length of the flexible connector 40. This allows the assembled combination of the flexible connector 40 and the plug 26 to be aligned within the patient's body by sliding the assembly over J-wire 12.

Deployment of the plug 26 and removal of the flexible connector 40 are depicted in FIGS. 3 and 4, showing the plug in relation to the Patent Foramen Ovale formed in the patient's atrial septum (AS).

The threaded end 44 of the flexible connector 40 and the threaded portion 32 of the plug 26 are threaded in the same direction. Thus, rotation of the flexible connector 40 by the wrench 46 in one direction, i.e., clockwise, first engages the threaded end 44 of the flexible connector 40 firmly within the tapped hole 38 of plug 26, and then engages the threaded portion 32 of the plug 26 in the tissue surrounding the PFO in the patient's heart. Once the plug 26 is deployed within the PFO, turning the flexible connector 40 by the wrench 46 in the opposite direction disengages the threaded end 44 of the flexible connector 40 from the tapped hole 38 of the plug 26, thus disconnecting the plug 26 from the flexible connector 40, and allows removal of the flexible connector 40 from the assembly of surgical kit 10.

Figure 2:
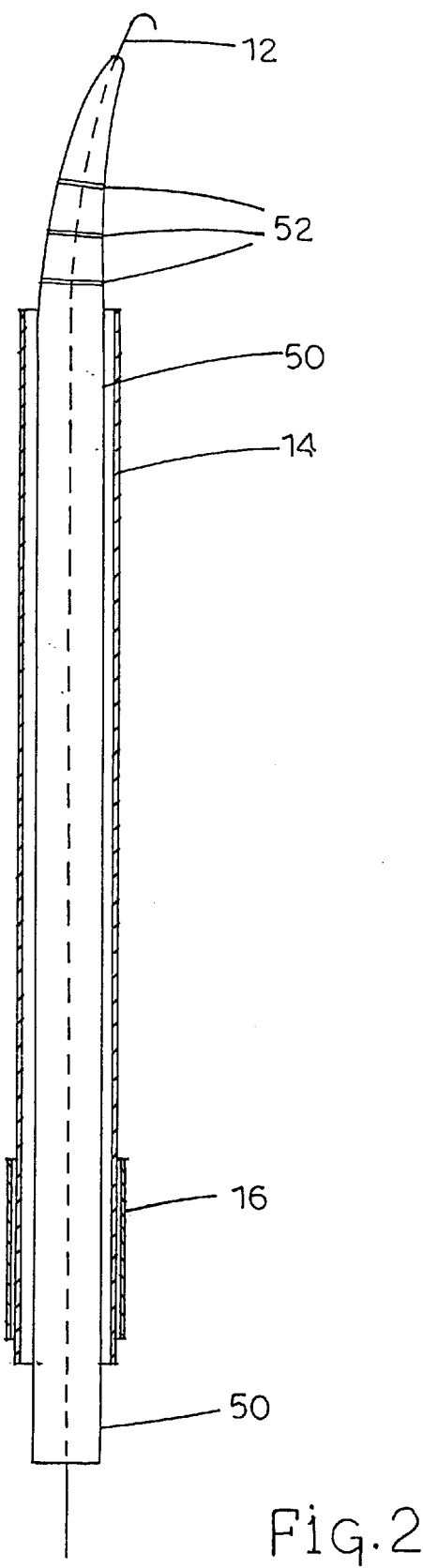
FIG. 2 is a section view of the surgical kit of the present invention illustrating the sizer.

FIG. 2 depicts a sizer 50 deployed within the catheter 14. Sizer 50 is a flexible elongate member that slides within catheter 14 and over J-wire 12. At its distal end, sizer 50 is tapered. Along the tapered portion, a plurality of markers 52 are formed in sizer 50 at calibrated diameters, e.g., 3 mm, 4 mm, and 5 mm. Markers 52 may be metallic bands or may be otherwise formed so as to be conspicuously visible via the imaging system used during the procedure. By sliding the tapered portion of sizer 50 along the J-wire 12 and into the patient's PFO until the increasing diameter of sizer 50 precludes further advancement, the size of the PFO can be estimated by observing the relative position of the calibration markers 52. In this way; the size of the PFO can be measured to a degree of accuracy sufficient to determine if it falls within a range of sizes for which the plug 26 will be effective.

FIGS. 5 and 6 depict the plunger 60 and its operation with the surgical kit 10 to extract the plug 26 from the plug carrier 22 following deployment in the PFO, for removal of the surgical kit 10. After the plug 26 is secured in the patient's PFO (formed in the AS), the flexible connector 40 is disengaged and removed, as described above. The plunger 60 is then introduced and advanced within the plug carrier 22, until it makes contact with plug 26. The length of plunger 60 is fixed relative to the plug carrier 22 such that when the plunger 60 first contacts the plug 26, the plunger finger tabs 62 extending radially therefrom at its proximate end are spaced a small distance from the proximate end of the plug carrier 22. This distance corresponds generally to the length of the plug 26 extending between the base 27 and the circumferential lip 30, i.e., the length of the plug 26 that is press-fitted into the distal end of the plug carrier 22, as shown in FIG. 5. When the plunger 60 is forced forward within the plug carrier 22, e.g., by utilizing the plug carrier tabs 24 and plunger tabs 62 in a manner analogous to the actuation of a hypodermic syringe, the plunger 62, abutting the plug 26 at its distal end, remains in a fixed position relative to the plug 26, catheter 14, and J-wire 12, and the plug carrier 22 is drawn a small distance towards the proximate end of surgical kit 10, thus disengaging it from the deployed plug 26. This is depicted in FIG. 6.

Turning to the method or process of inserting and securing the surgical plug 26 into a PFO in a patient's heart, reference is made to FIGS. 9–13. The surgical method of plugging a PFO described herein utilizes the surgical kit 10 described above. By using the surgical kit 10 and this surgical method, the need for thoracic surgery and its attendant risks, expense and recovery difficulties is obviated.

First the patient is positioned on a flouro-table, to enable the imaging device that will allow the surgeon to guide the catheter into the patient's heart and perform the method of the present invention. The patient is sedated and his or her right groin is prepared. The dilator 16 is introduced and secured to the patient.

Figure 9:
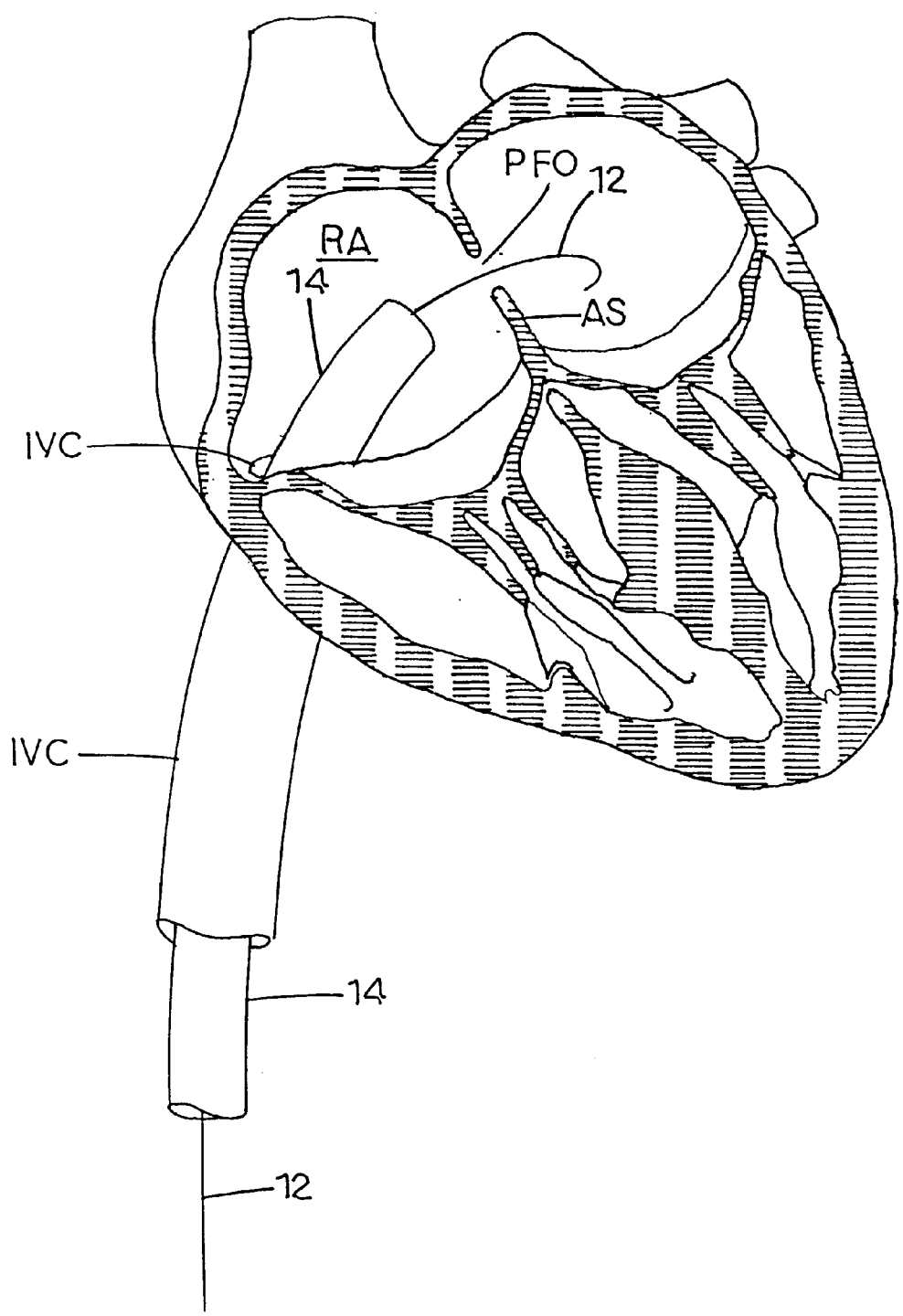
FIG. 9 is a section view of a heart with a Patent Foramen Ovale, depicting the placement of the J-wire and catheter.

The J-wire 12 of surgical kit 10 is then introduced into the inferior vena cava (IVC) at the right groin and guided up through the inferior vena cava into the right atrium of the patient's heart. The J-wire 12 is then positioned within the PFO in the patient's heart. The catheter 14 is then inserted around the J-wire 12, and advanced up through the inferior vena cava and into the right atrium (RA) adjacent the PFO formed in the AS. The catheter 14 and J-wire 12 are depicted in FIG. 9.

Figure 10:
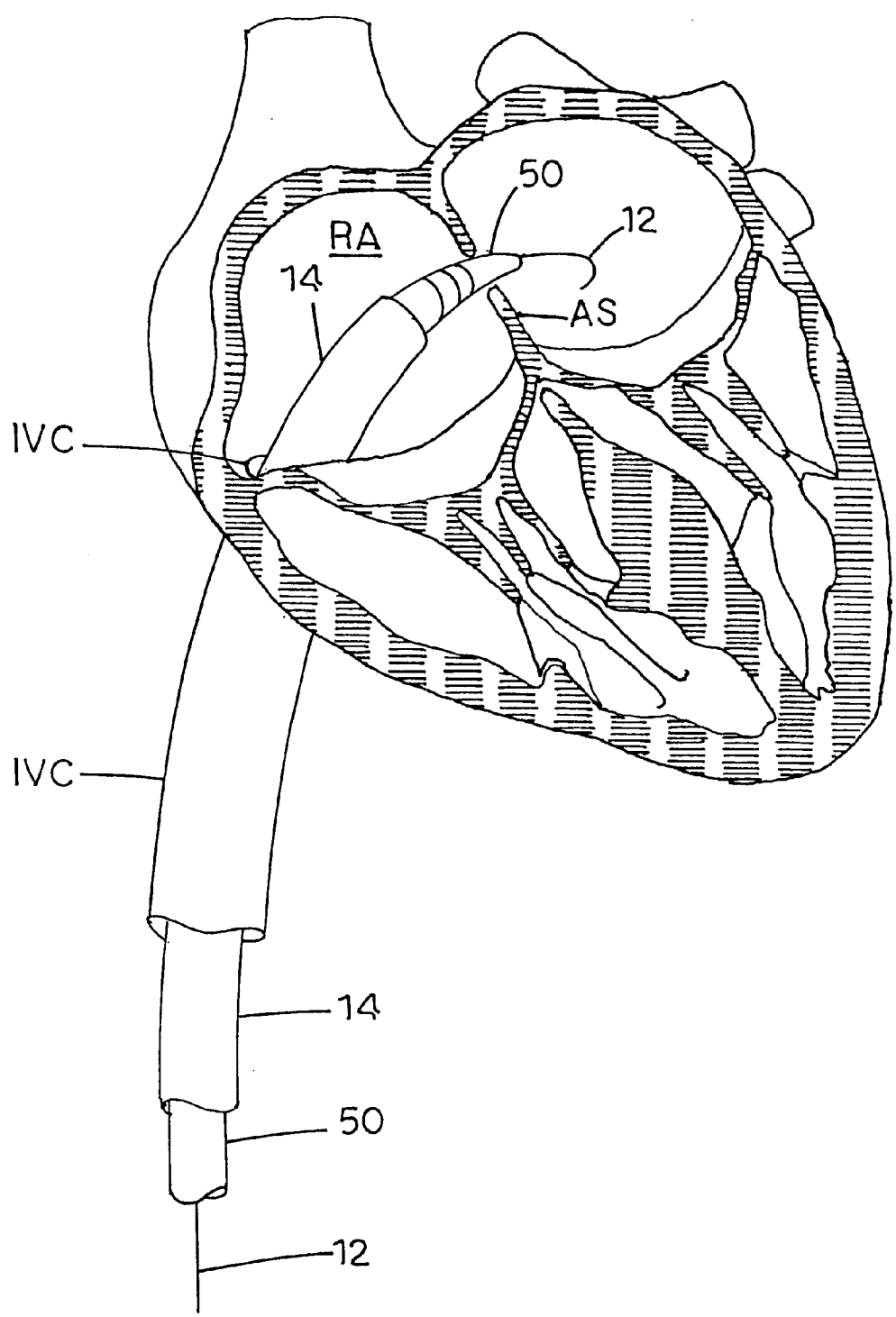
FIG. 10 is a section view of a heart with the sizer placed in the Patent Foramen Ovale.

Referring to FIG. 10, sizer 50 is threaded onto the J-wire 12 and advanced through the catheter 14, the tapered end thereof emerging from the catheter 14 in the patient's right atrium, and is guided by J-wire 12 into the PFO. The sizer 50 is advanced into the PFO until further motion is restricted by the increasing diameter of the tapered portion of the sizer 50. The surgeon then observes calibrated markers 52 and their position relative to the PFO on the surgical imaging system. The surgeon estimates the size of the PFO, and makes a decision whether to proceed. If the PFO is not in a predetermined range, e.g., approximately 3 mm to approximately 5 mm, the method of the present invention may be contraindicated and the catheter is removed. On the other hand, if the PFO is determined to fall within the appropriate size range, the sizer 50 is withdrawn from the catheter 14 and the surgical procedure is continued.

Figure 11:
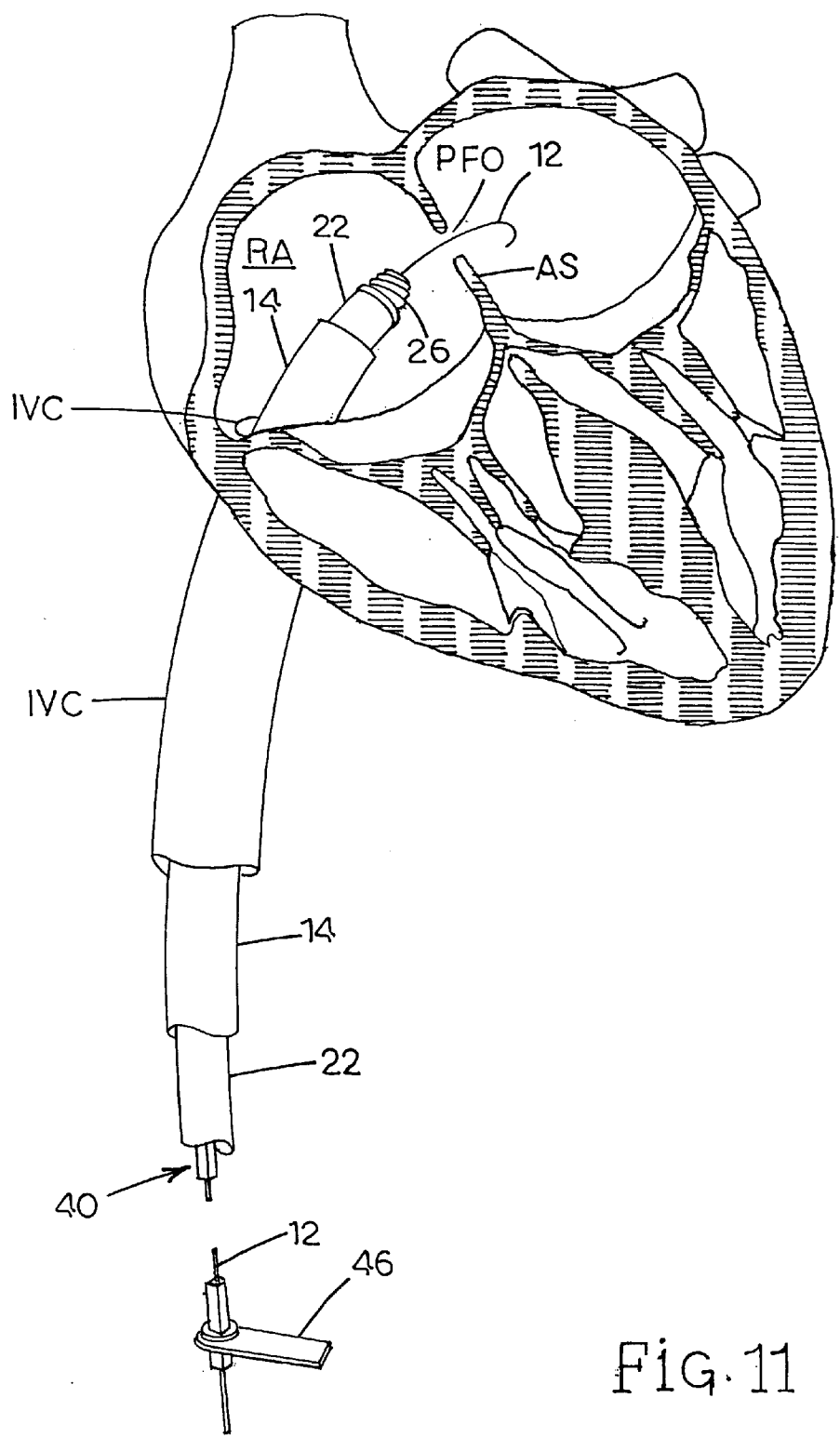
FIG. 11 is a section view of a heart showing the advancement of the plug in the plug carrier, with the flexible connector and wrench additionally shown.

As shown in FIG. 11, the plug 26, press fitted into the distal end of the plug carrier 22, and the flexible connector 40, attached to the plug 26 and disposed within the plug carrier 22, are advanced along the J-wire 12 and within the catheter 14 to a position adjacent to the PFO in the patient's heart.

Figure 12:
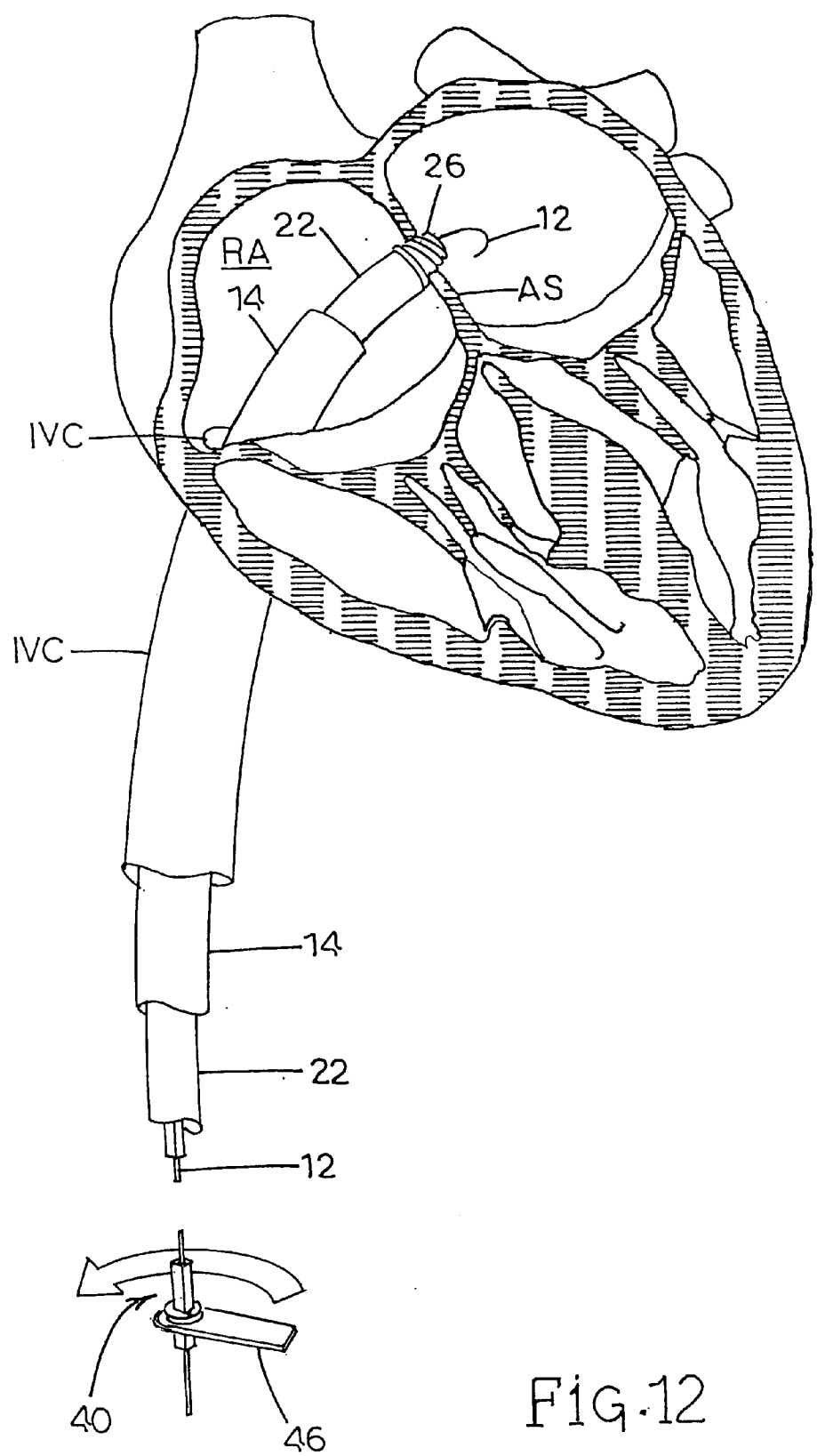
FIG. 12 is a section view of a heart depicting the deployment of the plug in the Patent Foramen Ovale, and indicating the operation of the wrench and flexible connector.

The plug 26 is guided into the PFO, and is rotated by actuating the wrench 46 on the flexible connector shaft 42 in the forward direction, e.g., clockwise, to advance the plug 26 into the patient's PFO, as depicted in FIG. 12. In one contemplated procedure, the flexible connector shaft 42 is rotated through approximately four complete revolutions or turns. This advances the plug 26 into the PFO by operation of the threads on threaded portion 32, bringing the circumferential lip 30 of the plug 26 into flush contact with the septum in the right atrium. The surgeon verifies the security of attachment of the plug 26 by gently tugging or wiggling the flexible connector 40, simultaneously feeling for motion and observing the deployed plug 26 via the surgical imaging system.

Thus deployed, the plug 26 is detached from the flexible connector 40 by rotating the flexible connector 40 in the opposite direction from that used to seat the plug 26, e.g., counterclockwise. This rotation may be facilitated by use of the wrench 46. It will be appreciated that in removing the flexible connector 40, only the flexible connector shaft 42 is rotated; the plug carrier 22 is not allowed to rotate. This is in contrast to the advancement of the plug 26, when the plug carrier 22 was allowed to rotate with the flexible connector shaft 42. The flexible connector 40 is rotated until the threaded end 44 completely disengages from the taped hole 38 in the plug 26, i.e., approximately 15 turns. The flexible connector 40 is then removed from the catheter 14.

Figure 13:
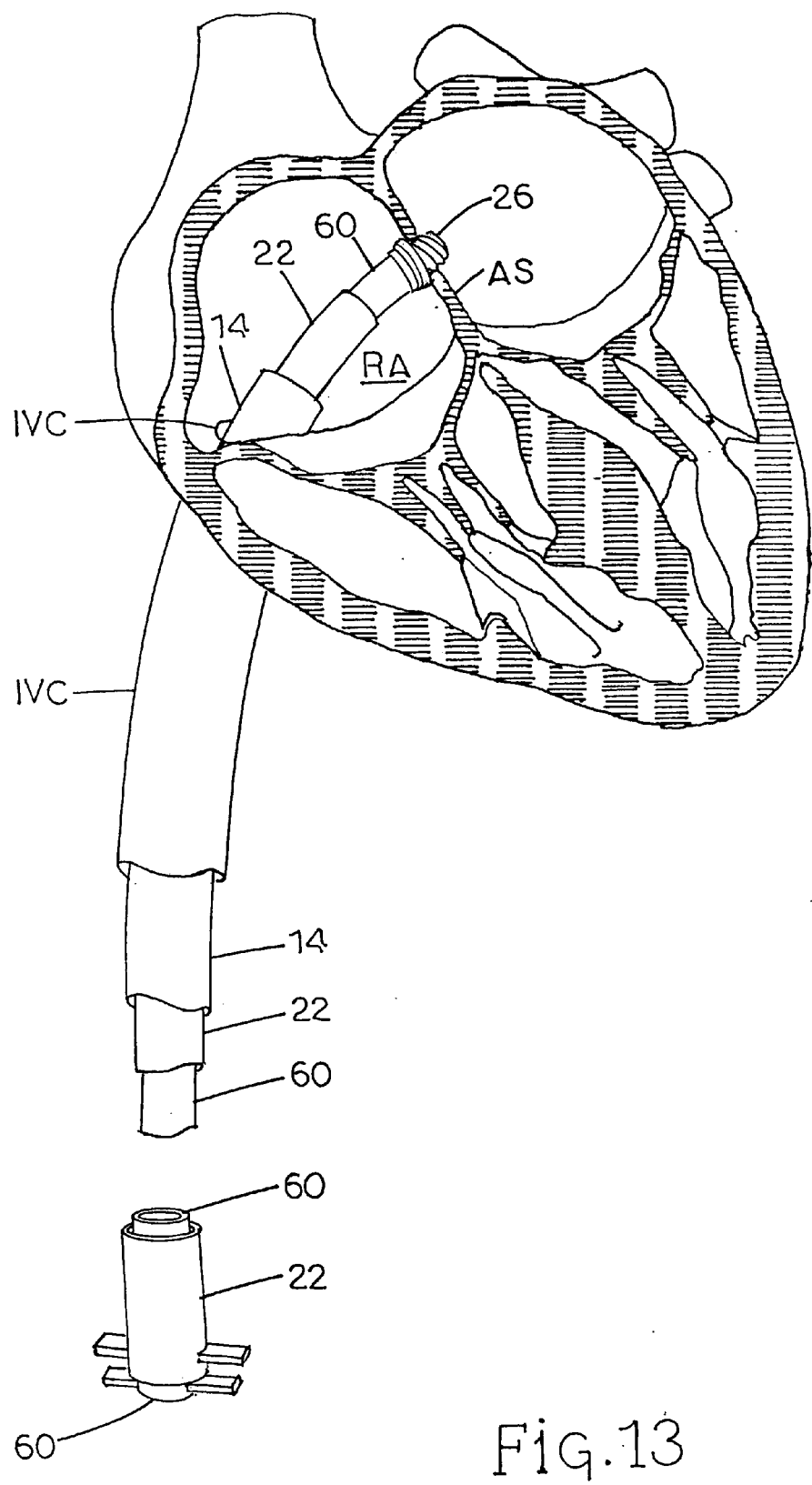
FIG. 13 is a section view of a heart showing the operation of the plunger to detach the plug carrier from the plug in the Patent Foramen Ovale.

Referring now to FIG. 13, the plunger 60 is next advanced over the J-wire 12 and within the catheter 14 until it contacts the base 27 of the plug 26. The plug 26 is then disengaged from the plug carrier 22 by pulling the plug carrier 22 off of the plug 26 via actuating the plunger 60. Grasping the finger tabs 24 at the proximate end of the plug carrier 22, and corresponding finger tabs 62 of the plunger 60, the plug carrier 22 and plunger 62 are pulled together. Since the distal end of the plunger 60 is abutting the base 27 of the plug 26, pulling the proximate end of the plunger 60 and the plug carrier 22 together results in pulling the plug carrier 22 off of the plug 26, thus releasing plug 26 from its press fit in the distal end of the plug carrier 22. The assembly comprising the catheter 14, the plug carrier 22, and the plunger 60 is then removed from the patient.

At this point, the security of the plug 26 within the PFO may be verified by having the patient cough and move from side to side. The surgeon observes the plug 26 via the surgical imaging system.

If for some reason the plug 26 is determined to be insecurely attached, improperly positioned, or manifests any other problem, the surgeon has the option of removing the plug 26. This is accomplished by reintroducing the catheter 14, the plug carrier 22, and the flexible connector 40 into the patient's heart, advancing the assembly over the J-wire 12. The plug carrier 22 is advanced to the base 27 of the plug 26. The flexible connector 40 is then advanced along the J-wire 12, entering the retrieval aperture 36 formed in the base 27 of the plug 26. The conical shape of retrieval aperture 36 guides the threaded end 44 of the flexible connector 40 into the taped hole 38 in the plug 26. The flexible connector shaft 42 is then rotated in a forward direction, e.g., clockwise, utilizing the wrench 46. When the flexible connector is firmly attached to the plug 26, the plug carrier 22 is advanced relative to the flexible connector 40, engaging the base end of plug 26 within the distal end of the plug carrier 22 in a press fit relationship. The plug carrier 22 and flexible connector 40 are then together rotated in a reverse direction, e.g., counterclockwise, thus disengaging the plug 26 from the patient's PFO. When the plug 26 is disengaged, the entire assembly may be removed.

If, on the other hand, the surgeon is satisfied that the plug 26 is sufficiently securely deployed and plugging the PFO, the J-wire 12 and the dilator 16 are removed from the patient, and the opening in the inferior vena cava at the patient's groin is closed. The patient then faces a brief and relatively painless recovery period of a few weeks, as opposed to the extended and traumatic recovery required following open-heart surgery.

Although the present invention has been described herein with respect to particular features, aspects and embodiments thereof, it will be apparent that numerous variations, modifications, and other embodiments are possible within the broad scope of the present invention, and accordingly, all variations, modifications and embodiments are to be regarded as being within the spirit and scope of the invention.

What is claimed is:

1. A method of plugging a Patent Foramen Ovale formed in a heart, comprising:
   inserting a threaded plug into the Patent Foramen Ovale; and
   rotating said threaded plug and securing said threaded plug in the Patent Foramen Ovale.

2. The method of claim 1, wherein said threaded plug is placed in the Patent Foramen Ovale via a catheter.

3. The method of claim 2, wherein said threaded plug is delivered to the Patent Foramen Ovale by a carrier that is advanced through said catheter.

4. The method of claim 3, further comprising decoupling said threaded plug from said carrier when said plug is secured in the Patent Foramen Ovale.

5. The method of claim 4, wherein decoupling said threaded plug from said carrier is performed by advancing a plunger through said carrier to said threaded plug, and contacting the threaded plug with the plunger and urging the threaded plug from the carrier.

6. The method of claim 3, wherein the step of rotating said threaded plug is performed by rotating the carrier secured to the threaded plug.

7. The method of claim 6, further including attaching a first member to said threaded plug such that during the procedure for plugging the Patent Foramen Ovale, both the carrier and first member are secured to the threaded plug and wherein the threaded plug is decoupled from both the carrier and the first member after the threaded plug has been secured within the Patent Foramen Ovale.

8. The method of claim 3 further including attaching a first member to said threaded plug such that during the procedure for plugging the Patent Foramen Ovale both the carrier and first member are secured to the threaded plug while the threaded plug is being advanced through the catheter to the Patent Foramen Ovale.

9. The method of claim 8 wherein the step of rotating said threaded plug is performed by rotating the first member which results in the threaded plug being screwed into the Patent Foramen Ovale.

10. The method of claim 1, wherein said,threaded plug may be removed from the Patent Foramen Ovale after insertion therein.

11. The method of claim 1, further comprising inserting a guide wire into the heart containing the Patent Foramen Ovale.

12. The method of claim 1, further comprising sizing the Patent Foramen Ovale, and terminating the procedure if the Patent Foramen Ovale is not within a predetermined size range.

13. The method of claim 1 further including:
   a. directing a guide wire into the heart and the Patent Foramen Ovale;
   b. inserting a catheter over the guide wire and extending the catheter towards the Patent Foramen Ovale;
   c. securing the threaded plug to a carrier, threading the guide wire through the carrier and threaded plug, and moving the carrier and threaded plug towards the Patent Foramen Ovale;
   d. securing a first member to the threaded plug, threading the guide wire through the first member, and moving the first member towards the Patent Foramen Ovale as the carrier is moved towards the Patent Foramen Ovale; and
   e. decoupling the threaded plug from both the carrier and the first member after the threaded plug has been secured within the Patent Foramen Ovale.

14. The method of claim 13 including the threaded plug into the Patent Foramen Ovale by rotating the carrier and the first member together.

15. The method of claim 14 including decoupling the threaded plug from the carrier and the first member after the threaded plug has been secured within the Patent Foramen Ovale.

16. The method of claim 15 including decoupling the threaded plug from the first member before decoupling the threaded plug from the carrier.

17. The method of claim 13 including inserting a sizer into the Patent Foramen Ovale to determine the approximate size of the Patent Foramen Ovale.

18. The method of claim 13 wherein the carrier includes a seat for receiving the threaded plug and wherein the threaded plug is press fitted into the seat.

19. The method of claim 18 wherein decoupling the threaded plug from the carrier includes inserting a second member into the carrier and contacting the threaded plug with the second member and urging the threaded plug from the seat of the carrier, thereby decoupling the threaded plug from the carrier.

20. The method of claim 19 wherein the first member secured to the threaded plug is threaded into a threaded bore formed in the threaded plug and wherein the first member is decoupled from the threaded plug by unscrewing the first member therefrom.

21. The method of claim 13 wherein the carrier includes a central opening and wherein the first member is extended through the central opening of the carrier while being secured to the threaded plug.

22. The method of claim 21 wherein the carrier includes a terminal end portion having a seat for receiving and holding the threaded plug.

23. The method of claim 22 wherein the threaded plug includes a tapped hole and wherein the first member includes a threaded end portion that is adapted to be secured into the tapped hole of the threaded plug.

24. The method of claim 23 wherein decoupling the threaded plug from the carrier and the first member includes first unscrewing the first member from the tapped hole within the threaded plug and then inserting a second member through the central opening of the carrier and contacting the threaded plug and urging the threaded plug from the seat formed on the terminal end of the carrier.

25. The method of claim 1 further including:
   a. inserting a catheter into the heart;
   b. securing the threaded plug to a carrier and inserting the carrier and threaded plug into the catheter and moving the carrier and the threaded plug through the catheter towards the Patent Foramen Ovale; and
   c. after securing the threaded plug into the Patent Foramen Ovale, decoupling the threaded plug from the carrier and removing the carrier from the catheter.

26. The method of claim 25 including securing a first member to the threaded plug and maintaining the secured relationship between the threaded plug and the first member as the carrier is moved towards the Patent Foramen Ovale.

27. A surgical kit for plugging an opening in a heart comprising:
   a. a threaded plug adapted to be secured into the opening in the heart;
   b. a carrier for holding the threaded plug and for delivering the threaded plug to the opening in the heart;
   c. a catheter for receiving the carrier and threaded plug and permitting the carrier and threaded plug to be moved therethrough to the opening in the heart; and d. a first member adapted to be removably secured to the threaded plug such that during certain times during the surgical procedure of plugging the opening in the human heart, both the carrier and the first member are connected to the threaded plug.

28. The surgical kit of claim 27 further including a second member for disengaging the threaded plug from the carrier.

29. The surgical kit of claim 28 wherein the second member comprises a plunger that is adapted to be inserted into the catheter for contacting the threaded plug and urging threaded plug from the carrier.

30. The surgical kit of claim 28 further including a sizer for measuring the approximate size of the opening in the heart.

31. The surgical kit of claim 30 wherein said sizer contains a plurality of indicia visible under a surgical imaging system wherein said indicia correspond to the diameter of said sizer.

32. The surgical kit of claim 31 wherein the sizer includes a tapered terminal end having a variable diameter.

33. The surgical kit of claim 28 wherein said threaded plug includes a tapped hole and wherein the first member includes a threaded end portion operative to be removably coupled with said tapped hole.

34. The surgical kit of claim 27 further including a guide wire adapted to lie interiorally of the threaded plug, carrier and catheter during a surgical procedure for plugging an opening in the heart.

35. A threaded plug for plugging an opening in a heart, comprising:
   a. a tip;
   b. a circumferential lip spaced from said tip and adapted to lie adjacent heart tissue surrounding the opening;
   c. a threaded portion disposed generally between said tip and said circumferential lip and including threads formed about an outer surface of the threaded plug; and
   d. a threaded hole for threadedly engaging and connecting to a first member.

36. The plug of claim 35, wherein the plug assumes a tapered configuration.

37. The plug of claim 36, wherein the taper gives rise to a plug diameter that becomes progressively smaller from the lip to the tip.

38. The plug of claim 35, further including a base portion opposite said tip.

39. The plug of claim 35, further comprising a tapered aperture formed adjacent said threaded hole and operative to guide said first member into said threaded hole.

40. The plug of claim 39 wherein the tapered aperture includes a relatively wide entry and from the relatively wide entry the tapered aperture becomes progressively smaller towards the threaded hole.

41. The plug of claim 35 including a cilia formed on the circumferential lip.

42. The plug of claim 35 wherein the tip is adapted to expand after the plug has been secured within the opening of the heart.

43. A surgical kit for plugging an opening in a heart comprising:
   a. a threaded plug adapted to be secured into the opening of the heart;
   b. a carrier for holding the threaded plug and for delivering the threaded plug to the opening in the heart;
   c. a catheter for receiving the carrier and threaded plug and permitting the carrier and threaded plug to be moved therethrough to the opening in the heart; and
   d. a guide wire adapted to lie internally of the threaded plug, carrier and catheter during a surgical procedure.

* * * * *